(12) United States Patent
Bischof

(10) Patent No.: US 8,691,245 B2
(45) Date of Patent: Apr. 8, 2014

(54) COMPOSITION FOR FORMING A TEMPORARY OBSTRUCTION AND METHOD OF FORMING THE SAME

(76) Inventor: Georg Bischof, Vienna (AT)

( * ) Notice: Subject to any disclaimer, the term of this patent is extended or adjusted under 35 U.S.C. 154(b) by 400 days.

(21) Appl. No.: 13/005,856

(22) Filed: Jan. 13, 2011

(65) Prior Publication Data

US 2011/0177021 A1 Jul. 21, 2011

Related U.S. Application Data

(60) Provisional application No. 61/294,597, filed on Jan. 13, 2010.

(51) Int. Cl.
| | | |
|---|---|---|
| *A61K 9/00* | (2006.01) | |
| *A61F 2/00* | (2006.01) | |
| *A61F 9/02* | (2006.01) | |
| *A61K 31/74* | (2006.01) | |
| *A61F 13/20* | (2006.01) | |
| *A61M 1/00* | (2006.01) | |
| *A61M 31/00* | (2006.01) | |

(52) U.S. Cl.
USPC ........ 424/400; 424/423; 424/436; 424/78.08; 604/48; 604/17; 604/27

(58) Field of Classification Search
CPC .......... A61K 47/00; A61Q 9/00; A61L 31/16; A61L 27/54; A61M 2205/02; A61M 2202/0007; A61M 2202/0014; A61M 2202/06; A61M 31/007
USPC ........... 424/400, 423, 436, 78.08; 604/48, 17, 604/27
See application file for complete search history.

(56) References Cited

U.S. PATENT DOCUMENTS

2003/0153866 A1* 8/2003 Long et al. ........................ 604/28
2007/0191768 A1* 8/2007 Kolb ............................ 604/104

FOREIGN PATENT DOCUMENTS

| CN | 1273860 A | 11/2000 |
|---|---|---|
| KR | 20020023441 A | 3/2002 |

OTHER PUBLICATIONS

GM Stiel, et al; "Peripheral embolism of hemostasis collagen (VasoSeal)", Z Kardiol, Oct. 1992; 81(10): pp. 543-545.
Jean Raymond, et al; "Temporary vascular occlusion with poloxamer 407", Biomaterials vol. 25, Issue 18, Aug. 2004, pp. 3983-3989.

\* cited by examiner

*Primary Examiner* — Abigail Fisher
(74) *Attorney, Agent, or Firm* — Drinker Biddle & Reath LLP

(57) ABSTRACT

The present invention relates to a method for forming a temporary obstruction of the intestine of a mammal, using a solidifiable composition, said composition being flowable and solidifiable to form a solid plug at a desired site within the intestine, the structure of said plug being changeable in order to allow for the subsequent, at least partial removal of the obstruction.

17 Claims, 3 Drawing Sheets

COMPOSITION FOR FORMING A TEMPORARY OBSTRUCTION AND METHOD OF FORMING THE SAME

The present invention relates to the field of medical endoscopy and endo-surgery, and, more specifically, the field of enteroscopy and entero-surgery.

For many years, endoscopy has been a well-established diagnostic procedure used in human and veterinary medicine. The endoscopes used for this procedure have been undergoing continuous development, and today they do not only allow for the simple illumination or imaging of the interior of the body, for example using optical fibers, but are also equipped for performing minimally invasive surgeries. Apart from fiber optics, modern endoscopes comprise, for example, air insufflators or gas pumps, irrigators, aspiration pumps as well as flexible tools, such as cannulae for injections, gripping or cutting tools, or wire electrodes for achieving coagulation by means of electrical current. The endoscope has several conduits for introducing the medical tools required for the respective surgical intervention.

Especially in the case of enteroscopic surgical interventions in the intestines of human beings and animals, complications often occur due to feces passing the location which is to be examined and/or to be treated surgically, in spite of previous administrations of laxatives, which does not only make the procedure more difficult and lengthier, but, in the case of surgical interventions, e.g. for obtaining tissue samples or removing tissue, also constitutes a risk of infection for the patient. Thus, it would be desirable to make it possible to seal the intestine for the duration of enteroscopic surgery.

In literature, the inventor only found WO 2008/103891, the main claim of which generally covers the formation of a polymer plug "at a site in a mammal" by letting a viscous polymer composition cure at body temperature, the only purpose of which described in the rest of the application, however, consisting in the closure of arteries, i.e. in hemostasis. The disclosure therein is based on reversely thermosensitive polymers, i.e. on polymers which are water-soluble at room temperature, but precipitate from the solution at body temperature. Examples include poloxamers, such as those marketed by BASF under the trade name Pluronics®.

Other literature references dealing with hemostasis using natural and synthetic polymers, in some cases additionally making use of the gelling of the polymer solution induced by changes in temperature, include: G. M. Stiel et al., Z. Kardiol. 81(10), 543-545 (1992) (using collagen as the polymer) and J. Raymond et al., Biomaterials 25, 3983 (2005) (poloxamers); CN 1273860 (Poloxamer 407); KR 2002/023441 (copolymers of N-isopropyl acrylamide); and U.S. Pat. No. 5,894,022 (albumin). The use of these materials for a closure of the intestine is neither mentioned nor proposed in any of the cited references. The first two references are also quoted in WO 2008/103891, wherein it is mentioned that the formation of a plug sealing a blood vessel under the influence of gelling is disadvantageous because, after its disintegration, such a plug entails the danger of sealing narrower vessels (referring to collagen in Stiel et al.) or undesirably disintegrates after a few minutes (referring to the poloxamers in Raymond et al.).

For the purposes of the present invention, such materials which can be caused to change their state due to a change in temperature are only suitable with reservations because, in the lumen of the intestine, having been essentially emptied before surgery, it would, contrary to the use in blood vessels, not be possible to warm the viscous polymer solution sufficiently fast for a polymer plug to form before significant proportions of the solution have flown past the site to be obstructed.

Against this background, the aim of the present invention consisted in providing a suitable material for the formation of a temporary obstruction of the intestine.

DISCLOSURE OF THE INVENTION

Thus, on the one hand, the present invention relates to a method for the formation of a temporary obstruction of the intestine of a mammal using a solidifiable composition, said composition being flowable and being solidified at a desired site within the intestine to form a solid plug, the structure of which is changed for a subsequent, at least partial, removal of the obstruction, and, on the other hand, to the composition as such. Such a composition of the invention may, for example, be pumped to the desired site via one or several conduits of a common endoscope and may then be solidified in situ, the way in which the composition is solidified and the way in which the plug is removed after the surgery has been completed not being subject to any specific limitations, as described in more detail below. The only essential aspect is that the plug is sufficiently stable for a sufficiently long period of time in order to form a barrier for the feces reaching the site in question so as to enable the physician to perform the endoscopic intervention downstream of the plug without any interference.

The plug does not necessarily have to form a complete obstruction (100%) of the intestine, but has to prevent at least semi-solid or solid feces from passing the site of the intervention, which means that the plug may, for example, also have a porous structure. Preferably, however, the passing of more fluid excrements is prevented as well, which requires a more compact consistency of the plug. As the width of the intestinal lumen to be obstructed varies widely (the small intestine having a width of about 2.5 cm, the colon having a width of about 6 cm, for example), the composition of the invention may, after its solidification within the intestine, have one of a number of different possible structures, depending on the desired requirement and the intended site of application within the intestine; said structures will be discussed in further detail below.

The composition preferably is a flowable solution, suspension, or dispersion of at least one natural or synthetic polymer and may preferably be solidified to form a solid plug by one or more methods selected from the group consisting of swelling, coagulation, polymerization, and cross-linking. In this way, it is, on the one hand, possible to transport the composition to the desired site of application within the intestine via a common endoscope and, on the other hand, its fast solidification at this site to form a plug, which is able to efficiently prevent excrements from reaching the respective site, can be guaranteed.

Swelling in water or another solvent or a mixed solvent constitutes a simple way of solidifying the composition which is also well tolerated by the patient; any organic solvents used should be physiologically safe in order to largely prevent irritations of the intestinal mucosa. Preferably, water or a aqueous mixed solvent is used. In some preferred embodiments, the composition may further be solidified to form a solid foam or a gel, as these can be produced fast and removed easily. The invention also comprises the solidification by means of polymerization or cross-linking as well as by means of the coagulation of solutions, suspensions, or dispersions of suitable compositions of the invention.

"Coagulation" or "flocculation" herein refers to the precipitation of a natural or synthetic polymer from a colloidal solution, a suspension, or a dispersion of the same. Polymers which swell in the course of their precipitation and thus form a gel obstructing the intestine are of special interest for the purposes of the present invention, which is why, for the purposes herein, the terms "coagulation" and "flocculation" encompass a simultaneously occurring swelling.

Examples of gel-forming polymers include gelatin, pectins, and other polypeptides, polysaccharides, such as starch, cellulose, agarose, tragacanth or gum karaya as well as other gums, mixed compounds consisting of polypeptides and polysaccharides, such as proteoglycans and glycoproteins, e.g. casein, but also nucleoproteins, lipoproteins, and other combinations of polypeptides and non-proteinaceous components, such as synthetic polymers, e.g. the so called "superabsorbers", i.e. polyacrylates and polyglycols, such as the poloxamers mentioned above, as well as derivatives of the compounds mentioned above.

Especially preferred are polymers, the solutions, suspensions, or dispersions of which occasionally show a viscoelastic or thixotropic behavior, i.e. which are flowable when energy is supplied, but re-solidify to form a solid gel, i.e. the plug, when the energy is withdrawn. Known examples of such polymers include liquid formulations of polyethylene glycol (PEG), polysaccharides, such as alginates, dextranes or cellulose ethers, e.g. carboxymethylcellulose derivatives, as well as some of the compounds listed above as gel-forming polymers.

The coagulation may occur spontaneously, for example when the liquid composition is exposed to certain conditions, for example when the respective values exceed or drop below specific threshold concentrations, temperatures, pH values, or ionic concentrations, or may be deliberately induced by the treating physician. Such an induction of the coagulation may, for example, be performed using a "gelling agent" which is defined below and may be included in the composition of the invention or transported separately, e.g. in the form of another flowable formulation, to the site of the obstruction. In the first case, in which the gelling agent is already contained in the (only) flowable composition, the pot life has to be kept in mind, i.e. the period of time, after adding the gelling agent, before the gelling effectively occurs. In the second case, in which the gelling agent is supplied separately, the composition of the invention constitutes a two-component system which, on the one hand, consists of the solution, suspension, or dispersion of the natural or synthetic polymer and, on the other hand, of the flowable formulation of the gelling agent.

"Gelling agent", as used herein in its widest sense, refers to any agent which leads to the gelling of the composition of the invention. This includes both gelling agents of the narrower definition, i.e. the gel-forming polymer itself as well as other macromolecules which are often referred to as "thickeners", and coagulating, flocculating or precipitating agents, such as salt solutions which sufficiently change the ionic concentration or the zeta potential of the polymer solution or suspension in order to induce a coagulation and a simultaneous gelling of the polymer. As mentioned above, a two-component system may sometimes also consist of two formulations, i.e. (colloidal) solutions, suspensions, or dispersions, which have different concentrations of the polymer to be coagulated and which, when mixed, provide a concentration at the site of obstruction such that the polymer coagulates, precipitates, and, at the same time, gels to form the desired plug.

The "site of obstruction", as used herein, refers to the site at which the intestine is to be temporarily obstructed. Due to the flowability of the compositions of the invention, they sometimes have to be transported to a position which is situated slightly above the later position of the solidified plug, which is why the definition of the site of obstruction includes a range of variation, for example of about 10 cm. Additionally, it is clear to those skilled in the art that, in all cases covered by the invention, the composition should be solidified as fast as possible in order to largely prevent it from flowing away from the desired position. Thus, most of the compositions of the invention should have a viscosity which makes them just flowable, in order to make it possible to pump them into the intestine, but which makes them solidify fast in situ, preferably within seconds. Exceptions include, for example, viscoelastic or thixotropic compositions, the viscosity of which in the flowable state also depends on the amount of energy supplied.

In especially preferred embodiments, polymers which are further swellable after their coagulation or "infinitely" swellable are used in order to initially gel to form a gel plug in the course of the first swelling which, in the case of the addition of additional swelling agent, which preferably is water, is dissolved and thus removes the obstruction. Suitable examples include gelatin, agar(-agar), carrageen, furcellaran, and similar compounds as well as derivatives thereof. The destruction of the plug by means of (sometimes repeated) swelling will later on be described in further detail.

"Polymerization", as used herein, refers to any reactions forming macromolecular chains of polymerizable monomers or prepolymers, "cross-linking" referring to a special case of such a polymerization reaction in which two or more polymer chains are linked to form a three-dimensional polymer network. The monomers and prepolymers which can be used for this purpose are not subject to any special limitations, but for obvious reasons physiological safety constitutes a decisive criterion. Above all, they should not cause irritations of the intestinal mucosa and should not be resorbable by it. Monomers or prepolymers which, in the course of the degradation of the polymer obtained from these—which may even be desired or deliberately induced—yield metabolites which are useful as nutrients and the resorption of which is desirable constitute exceptions in this respect. There are numerous examples including lipids, proteins, and carbohydrates, which may be transformed into the desired monomers or prepolymers by means of preceding modifications with polymerizable groups such as ethylenic double bounds. Due to the high number of possible compounds, only carbonic vinyl ester of mono- and polysaccharides which, when the vinyl group is polymerized, yield polyvinyl alcohol derivatives which can be easily cleaved will be mentioned as an example. The polyvinyl alcohol resulting from the cleaving of the carbonate ester is metabolically inert, while the polysaccharide is enzymatically digested into monosaccharides which can be utilized by the body and resorbed in the intestine.

It is preferable to use monomers or prepolymers being polymerizable to form polymers which swell in the water in the intestinal secretion at the intestinal mucosa or in a solvent which may be used, if necessary, in order to better adapt to the width of the intestinal lumen to be obstructed.

The way in which the polymerization is carried out—as well as the way in which the disintegration of the plug produced by the composition in the intestine—significantly depends on the site of use, as the intestinal flora and the chemical composition of the intestinal secretions vary considerably in the individual intestinal sections (small intestine, colon) and subsections (duodenum, jejunum, ileum; caecum, colon, rectum). Thus, the composition of the invention has to be adapted to the specific area of use with its respective chemical environment.

The way in which the polymerization is performed is not subject to any specific limitations, so that, in general, anionic, cationic and radical polymerization, polycondensation, polyaddition, ring-opening polymerization, etc. may be applied. As it is desirable that the polymerization rate is as high as possible, radical polymerization constitutes, above all, the method of choice and is preferred according to the invention. The radical polymerization may be initiated thermally or photochemically, which, in both cases, may be induced by means of irradiation via the optical fiber of a conventional endoscope. A sufficient amount of a sufficiently viscous polymerizable composition may, for example, be pumped to the desired site via a conduit of an endoscope and may then immediately irradiated with light, e.g. infrared radiation for thermal initiators or UV/VIS radiation for the majority of common photoinitiators, via an optical fiber in another conduit of the endoscope in order to induce the polymerization. Preferably, radical initiators, which generally may be selected from Type-I initiators, i.e. alpha-cleavage initiators such as benzoine, acetophenon, benzilketal, and acyl phosphine oxide derivatives, and Type-II initiators, i.e. hydrogen abstractors such as benzophenon, quinone, diketone and thioxanthone derivatives, are used in this connection.

The usually relatively low depth of penetration of radiation into the polymerizable composition also has to be kept in mind; thus, the layers' thickness should, for example, not exceed about 2 cm in the case of polymerizations using UV-active photoinitiators. For this reason, photopolymerization or thermal polymerization using infrared radiation initiation is not preferred in areas with a relatively wide intestinal lumen, i.e. in the colon, for example.

As long as all components of the polymerizable composition are innocuous for the tissues they contact before they are polymerized, the duration of the polymerization reaction is only of secondary importance. As it is required that the composition is flowable and due to the resulting problem that part of the composition might flow away, as mentioned above, the polymerization should make enough progress within a few seconds to ensure that the polymerized portion of the composition is able to keep the remaining composition at the predetermined obstruction site until the polymerization is essentially completed.

The polymerizable composition may contain a solvent which preferably is water or an organic solvent tolerated by the body, or a mixture thereof. However, as the viscosity should be as high as possible while the composition should also be flowable and have as high a polymerization rate as possible, the composition sometimes is solvent-free. In such cases, all or some monomers may serve as reactive diluents which become integrated into the polymer formed in the course of the polymerization, and the thus formed polymer should be swellable with the water contained in the intestinal secretion, at least in the peripheral areas of the plug.

According to the invention, it is preferable for the composition of the invention to contain monomers or prepolymers which are not only well tolerated before their polymerization, but also after their structure has been changed or after the polymer plug has been destroyed again. It is especially preferred that the compositions are compounds which are inert in the case of a possible—or desired—disintegration of the polymer within the intestine, or which may serve as nutrients which can be resorbed by the mucosa. Examples of the first case include vinyl ester polymers which form polyvinyl alcohol as a side product after polymerization and cleavage of the ester bound, said polyvinyl alcohol, due to its inertness, being part of numerous drugs (e.g. as a protective colloid). Examples of the second case may be selected from a wide variety of polysaccharides, polypeptides, and lipids, so that only glycogen and gelatin will be mentioned as possible examples of polysaccharides and polypeptides herein.

As mentioned above, the composition has to be solidifiable to form a plug, the structure of which is changeable for a subsequent, at least partial, removal of the obstruction, said structural change being an at least partial mechanical, physical and/or chemical destruction. Herein, an at least partial destruction of the structure, in its widest sense, refers to any structural change of the plug, which enables a greater amount of feces to pass the site than immediately after the formation of the intestinal obstruction at said site. Such a structural change may occur spontaneously and/or may be induced by external influences; said "spontaneously" occurring changes may be triggered by the conditions within the intestine, e.g. by the pH value of the intestinal mucosa or enzymes secreted into the intestine.

A "mechanical destruction of the plug structure" includes any measure taken by the treating physician using suitable tools by which the intestinal obstruction is at least partly removed and by which the structural integrity of the plug is preferably affected or destroyed. To this end, the different gripping or cutting tools with which common endoscopes are usually equipped or equippable may be used in the way already described above, or special tools may be configured for this purpose. Thus, depending on its structure, the plug may be severed by means of a forceps or a scalpel, may be torn apart by means of a gripper or pierced by means of a pin in order to at least partly remove the obstruction of the intestine.

The invention also comprises gripping the plug with a gripping tool mounted to one end of the endoscope after completing the endoscopic surgery and, subsequently, pulling the—sometimes essentially intact—plug out of the intestine via the anus. In this case, the above requirement of a changeable structure of the plug in order to at least partially remove the obstruction means that the plug material should have an elastic flexibility and, at the same time, be sufficiently consistent in order to allow for the obstructing plug to be removed from the intestinal wall and transported through the intestine, without causing any injury to the mucosa. The invention also encompasses cases where the plug is gripped with a tool and removed from the intestinal wall and is then transported to the anus by the pressure exerted on the plug by the following feces, instead of being transported there manually. Due to the risk of a new, undesired obstruction of the intestine occurring on the way to the anus, this embodiment is not preferred, though.

A mechanical destruction of the plug, followed by its disintegration is also possible; the disintegration may occur spontaneously or may be initiated by the treating physician and may be carried out more or less fast. A preferred example provides that a plug formed due to its viscoelastic or thixotropic behavior is re-converted into its flowable state by supplying mechanical energy in the form of shear stress to the plug, i.e. by penetrating into it and performing a stirring motion, optionally exerting a low pressure on the intestinal wall, which results in at least part of the plug material flowing away from the obstruction site, thus removing the obstruction, the plug material being subsequently gradually disintegrated by the intestinal secretion and finally removed via the anus or resorbed by the intestinal mucosa. The at least partial resorption constitutes a preferred variety in all cases in which the plug is removed.

Physical structural changes of the plug include all processes which, without using any tools, sufficiently change the structure in order to at least partially remove the intestinal obstruction without any substantial chemical changes of the plug material. This, for example, includes structural changes due to an increase or a decrease in temperature. For the purposes herein, swelling and shrinkage, meaning the reverse process of swelling, are also included in the widest sense of the definition, even though these processes inevitably lead to significant changes of the state of chemical bonds within the plug material.

Temperature changes brought about by the treating physician may, for example, be caused by irradiating the plug with infrared light; again, using appropriate light sources, optical fibers provided in modern endoscopes may be used for this purpose, even though better results can be achieved when special optical fiber cables adapted to the infrared range are used.

Even though a spontaneous swelling/shrinkage due to the conditions within the intestine, for example due to the influence of feces reaching the plug, is not excluded, these processes usually require the targeted supply of a reaction partner, i.e. a swelling agent such as water or a solvent or a shrinking agent or "anti-swelling agent", i.e. of an agent which makes a swollen polymer (e.g. a hydrogel) reduce its degree of swelling and thus its volume. Salt solutions or other solutions or suspensions of ionic solutes entering into the swollen polymer and saturating its secondary valences so that they can no longer bind any water or solvent, which leads to a reduction of the degree of swelling and causes the plug to shrink, may, for example, be used as shrinking agents.

The structure of the plug may preferably be at least partially destroyed by swelling or—if the composition of the invention has already been solidified by swelling in order to form the plug—further swelling, so that the supply of a swelling agent or of an additional swelling agent is sufficient in order to bring about the desired structural change. The additional swelling agent may be the same agent as the one used for the first swelling process or another agent. The first swelling for solidifying the composition of the invention may, for example, be carried out using water, while the structure of the thus formed plug may then be (at least partially) destroyed again by using an aqueous mixed solvent as a second swelling agent, or vice versa.

The structural change brought about by swelling may include both the plug material's—more or less complete—dissolution and its mere softening, so that it may be easy (or easier) to mechanically destroy the (again) swollen, soft plug, or the plug material may be softened to such an extent that the plug is transported out of the intestine naturally by means of the pressure of the feces reaching the site, without the risk of a new obstruction of the intestine occurring on the way to the anus. The latter variation thus constitutes an example of a structural change including a combination of a physical or physico-chemical destruction and a mechanical removal.

Alternatively or additionally to the above described swelling, the structure of the plug may also be at least partially destroyed by being irradiated with electromagnetic radiation. The composition of the invention may, for example, comprise a polymer which contains a photo acid generator releasing an acid when irradiated with light of an adequate wavelength, which induces the desired structural change of the plug. The polymer may, for example, also contain a photoinitiator inducing polymerization or cross-linking within the plug material when irradiated and thus causing a structural change of said material. The structural change may, for example, consist in the generation of a (more) porous and thus more permeable polymer network or of a material showing increased swellability by means of such a photopolymerization of the plug material. The latter case is an example of a structural change brought about by a combination of irradiation and swelling.

Alternatively or additionally to swelling and irradiation, the structure of the plug may also be at least partially destructible by cleaving chemical bonds; herein, in order to distinguish this definition from the above definition of physical structural changes, the term "cleavable chemical bonds" mainly refers to covalent bonds, since, in the course of swelling or shrinking, but also of coagulation processes, secondary bonds such as coordinative bonds, e.g. hydrogen bonds, or ionic bonds are "cleaved".

For cleaving such chemical bonds, the composition of the invention preferably comprises one or more polymers and/or one or more monomers containing labile bonds, which monomers are to be polymerized to form a polymer network when the composition is solidified by polymerization or cross-linking. "Labile bonds", as used herein in its widest sense, refers to a bond which can be chemically cleaved in a relatively simple way and preferably under mild conditions. Labile bonds are preferably selected from hydrolysis-, light- and temperature-sensitive bonds, preferably from the group consisting of acetal, ketal, ester, ortho-ester, azo, ether, and anhydride bonds. Enzymatically cleavable bonds are also preferred, and bonds which can be cleaved by digestive enzymes produced in the body and secreted in the intestine are especially preferred, the type of the bond again depending on the intended site of the surgery and thus of the obstruction.

For example, it is possible to generate an acid by irradiating one of the abovementioned photo acid generators, which then causes the cleavage of acid-labile bonds within the plug, thus constituting an example of a structural change brought about by a combination of irradiation and the cleavage of chemical bonds. For reasons of physiological harmlessness, any acid released by a photo acid generator under the influence of irradiation or deliberately added, e.g. as a reagent (solution), should not be too strong, which is why the labile (in this case: acid-labile) bonds should already be cleavable in a slightly acidic medium. This analogously also holds true when bases are used to cleave base-labile bonds, which also constitute examples of hydrolysis-sensitive bonds.

For this reason, compounds with acid- or base-labile bonds which are even cleavable in the presence of dilute acids or bases are especially preferred, such compounds including carbonates, acetals, anhydrides, and ortho-esters. This way, one can obtain a plug material which is cleavable by the chymus or the feces at the slightly acidic or slightly alkaline pH values thereof, which depend on the composition of the food metabolized by the mammal and the location of the site of the surgery within the intestine; consequently, the plug gradually disintegrates, at least partially, even without external interference. For example, the pH value varies between about 5 and 8 in the duodenum and between 5.5 and 6.8 in the colon. In practice, the pH value of the intestine at the intended site of the obstruction may be controlled to a certain extent by administering to the patient a diet specifically adapted for this purpose over a certain period of time before the intervention.

Compounds with light- or temperature-sensitive bounds such as azo and diazo groups are also preferred for a photolytic or thermolytic change or destruction of the structure of the plug formed by the composition of the invention. In both cases, the change/destruction may again be triggered by irradiation via the optical fiber of the endoscope.

A significant advantage of the composition of the invention consists in the fact that it may be supplied to the desired site via the anus, for example by pumping it, via a conduit of a conventional endoscope, to the site of use where it is solidified in an adequate way in order to form said plug. Thus, using the composition of the invention, no trauma of the intestinal wall is required in order to achieve the obstruction of the intestine. The obstruction of the intestine may be achieved in a non-invasive or minimally invasive way (depending on the definition applied) and in a way which is very well tolerable for the patient undergoing treatment.

Preferably, the solid plug formed by the composition of the invention is also removed via the anus, optionally after a previous, at least partial, destruction of its structure. If said at least partial destruction of the plug's structure involves a chemical or biological degradation, an at least partial resorption via the intestinal wall of the patient may also take place, alternatively or additionally to the removal via the anus.

In addition to the components required for forming the plug, the composition of the invention may contain any further components as long as they do not make an application in the intestines of mammals impossible and do not interfere with the effect of the invention. Examples to be explicitly specified herein include viscosity modifiers such as thickeners or flowing agents, solubilizers or solubility promoters, e.g. surfactants and emulsifiers, gelling agents, foam stabilizers, and adhesives. The latter serve the purpose of promoting an improved adhesion of the plug to the intestinal wall, for which, for example, intensely sticky natural polymers may be used, e.g. the above-mentioned tragacanth and karaya gums. They may be merely mixed into the composition, for example if the plug is formed solely as a result of swelling, or may be modified in a way such that they participate in possible polymerization reactions. In this case, such derivatives may represent the only polymerizable compounds and may be polymerized to homopolymers forming said plug, or they may form copolymers with other polymerizable components of the composition.

The patients to whom the composition of the invention is to be administered are not subject to any particular limitations and may be pet or domestic animals. However, not least because of the quite considerable costs of endoscopic interventions, the patients will normally be human patients.

Figure 1:
FIGS. 1 to 3 show photographs of a model experiment of the implementation of the invention in a natural porcine intestine.

Below, the present invention will be further described referring to non-limiting example cases and specific model experiments using porcine intestinal sections referring to the figures.

EXAMPLES

As both the components as well as the characteristics of the compositions of the present invention are significantly influenced by the way in which the polymer plug forming the obstruction is formed as well as by the way in which said plug is removed, the examples below are grouped according to these procedural aspects. Examples 1 to 13 describe different types of solidification for forming a plug, while the subsequent examples 14 to 28 illustrate the removal of the obstruction; in practice, any combination of methods of forming and removing a plug are possible, even though this might not be explicitly stated for each and every case in the examples below. In all examples, the compositions of the invention are supplied to the site of the obstruction in a simple way via the conduits of an endoscope, even though, at least theoretically, there are other options for transporting the respective composition to the obstruction site, for example via separate tubes or conduits or, for example, by means of a syringe via the intestinal wall. Due to the complexity resulting therefrom, such interventions are hardly used in practice.

As mentioned above, compositions of the invention may contain any additional components, the average artisan in the field of medical chemistry being easily capable of formulating suitable formulations the components of which are compatible with each other and thus tolerable for the intestinal mucosa contacted by them.

A) Different Ways of Forming an Obstruction of the Intestine

A1. Solidification of the Composition by Gelling/Coagulation

Examples 1 and 2

Two-Component Systems

An aqueous colloidal solution or suspension of a swellable polymer at a concentration close to the gelling point, referred to as formulation A, is pumped via a conduit of a conventional endoscope to the desired site of obstruction. Via a second conduit of said endoscope, a sufficient amount of a flowable formulation B of a gelling agent is dispensed to the same site in the intestine. The viscosities and the pumping pressure are selected in a way that, on the one hand, the two formulations may be transported quickly to the target site in order to prevent too strong a change in the temperature of the respective formulation in the conduit and that, on the other hand, a quick mixing of the two formulations can be ensured in order to prevent significant amounts of the two liquids from flowing away from the obstruction site.

Example 1

The Polymer Itself Serves as a Gelling Agent

The formulations A and B are colloidal solutions of agar-agar, gelatin, carrageen or the like, which, optionally, have been chemically modified, said optional modification serving, for example, to achieve a shift of the temperature at which the transition from the gel to the sol states takes place, hereinafter referred to the "gelling temperature", said temperature normally amounting to 35° C. in the case of gelatin and to 45° C. in the case of agar-agar, or to improve the solubility, as otherwise solid gels may already be formed of 1% solutions. Alternatively or additionally, a surfactant such as a non-ionogenic surfactant, e.g. a copolymer of ethylene oxide and propylene oxide, or another suitable agent may be added as solubility promoters having the effect that the gelling only takes place at higher concentrations.

If no such solubility promoters are added, formulation A may be an aqueous solution at a concentration just below the gelling point, e.g. a maximally about 0.9% solution, while formulation B may be an aqueous solution at a higher concentration which is heated to a temperature above the gelling temperature, said higher concentration depending on the quantitative and the mixing ratio of the two components. For example: 100 ml of a 0.9% formulation A and 10 ml of a warm 15% formulation B are simultaneously supplied to the obstruction site. "Warm", as used in this connection, refers to a temperature which is sufficiently high in order to ensure that, in spite of possible cooling within the endoscope's conduit, the solution has a temperature above the gelling temperature when being discharged from the endoscope into the intestinal lumen, in order to prevent it from gelling within the conduit. Depending on the flow rate, the length of the flow path, and the extent of heat exchange between the transported solution and the material of the conduit, a temperature of 50 to 60° C. at the point of entry into the conduit should be sufficient. Preferably, the temperature only lies slightly, for example by <5° C., above the gelling temperature at the point of discharge, so that the cooling may take place sufficiently fast in order to form the plug and in order to prevent excessive amounts of the solution from flowing further downstream.

The two solutions yield a mixture at a concentration above the gelling concentration and a temperature below the gelling temperature, so that the polymer immediately forms a solid gel plug with a diameter of about 4 to 5 cm, which plugs the intestine at the respective site.

Alternatively, water or physiological saline may be used as formulation B. In this case, the gelling will be initiated by pumping a solution of the polymer at a concentration which lies significantly above the gelling value, e.g. a 5% solution, and at a temperature above the gelling temperature as the formulation A to the obstruction site, and by supplying water at room temperature or at a lower temperature, e.g. 10 to 15° C., in order to quickly form a mixture at a temperature below the gelling temperature.

Example 2

Additional Gelling Agent

Formulation A is an about 0.9% solution of gelatin, agar-agar, or a similar, optionally modified polypeptide or polysaccharide, as described in example 1, and formulation B is a solution of a separate gelling agent, such as saturated saline. Upon mixing the two components, the solubility of the polymer is lowered by the salt, so that the polymer coagulates and gels to form the desired plug.

Examples 3 to 6

One-Component Systems

Using similar mechanisms as those described above for two-component systems and/or rheological effects, the invention may also be implemented in the form of a single flowable composition.

Example 3

Gelling Due to a Spontaneous Change in Temperature

A solution of one of the above-mentioned polypeptides or polysaccharides at a concentration above the gelling value is supplied into the intestine in a heated state, i.e. at a temperature which is sufficiently high, so that the solution reaching the obstruction site has a temperature slightly above the gelling temperature. In the course of cooling down, the composition gels and forms the obstruction.

Alternatively, however, solutions or suspensions of polymers may be used, for which the change from the sol state to the gel state occurs in the case of temperature changes in the reverse direction, i.e. they gel when they are heated. Examples include poloxamers which are known according to the state of the art and have already been mentioned at the beginning, said poloxamers being supplied in the form of cold solutions, e.g. at a temperature of about 15° C., and gelled when being heated to the respective gelling temperature, e.g. 20° C. However, it has to be taken into consideration that gelling under heating usually takes place significantly slower than gelling under cooling, so that this variation is not preferred according to the invention.

Example 4

Gelling Due to Targeted Heating

The above-described problem in connection with polymers gelling in the case of an increase in temperature may be solved by an additional heating of the solutions in situ. As mentioned in example 3, a solution at a temperature of about 15° C. may be pumped to the obstruction site and immediately irradiated with infrared light via the optical fiber of the endoscope in order to cause sufficiently fast heating and thus the gelling of the solution. This example illustrates the formation of a plug by combined gelling and irradiation.

Example 5

Gelling Due to Dehydration

An about 0.9% gelatin solution or a similar solution, as described in example 1, which has optionally been adjusted, by adding a thickener such as a cellulose ether, e.g. hydroxyethyl cellulose, or polyvinyl alcohol, to such a viscosity that it is still just flowable at body temperature, is pumped to the obstruction site. The composition is preferably pre-heated to body temperature before being introduced into the endoscope's conduit. Due to the resorption of water from the composition in the intestine, its viscosity is further increased until its concentration exceeds the gelling threshold and it gels to form the plug.

Example 6

Gelling to Due Viscoelasticity or Thixotropy

In this case, a colloidal solution, suspension, or dispersion of a natural or synthetic polymer which is well tolerated by the body and shows a viscoelastic or thixotropic behavior is used. The formulation preferably contains one or more suitable polymers, such as polyethylene glycols, polysaccharides, e.g. alginate, dextran, or cellulose ethers, e.g. carboxymethylcellulose derivatives, at such concentrations that, if no external energy is supplied, the formulation is not flowable, but may be pumped through the endoscope's conduit when a small amount of energy is supplied. Additionally or alternatively, the formulation may contain a certain amount of a (further) physiologically safe thixotropic agent.

In practice, a solution, suspension, or dispersion of a suitable polymer in gel form is liquefied by stirring and pumped through a conduit of the endoscope to the obstruction site at such a pressure and flow rate that the resulting shear stress provides sufficient energy in order to maintain the flowability of the formulation. After discharge from the conduit, the energy is not supplied any longer and the formulation quickly solidifies to form a solid gel obstructing the intestinal lumen.

A2. Solidification of the Composition by Means of Polymerization

Examples 7 to 10

One-Component Systems

In these cases, a polymerizable composition of the invention is pumped to the obstruction site as a formulation and is solidified by polymerization to form a solid plug. In all cases, the polymerization essentially only takes place in situ, i.e. at the obstruction site, but it may already set in during the composition's transport through the conduit, as long as the composition remains flowable. In general, it has to be stated again for all polymerization examples—including both one- and two-component systems—that the polymer formed by polymerization should be swellable with an optionally present solvent or with water from intestinal secretions or with both.

Example 7

Polymerization at Room Temperature

A polymerizable formulation is formed by mixing a suitable monomer or prepolymer with an initiator being already reactive at room temperature and, optionally, a solvent, preferably water. In this case, suitable initiators include mainly redox initiators of free-radical polymerizations, e.g. the systems $Fe^{2+}/H_2O_2$, peroxysulfate/metabisulfate, peroxide/thiosulfate, or peroxysulfate/thiosulfate, all of which are water-soluble. For the graft polymerization of different polysaccharide derivatives such as modified cellulose, the use of, for example, a cerium(IV) salt is sufficient, as the polysaccharide itself serves as the reductive redox partner. Anionic and cationic initiators may also be used, but are not preferred due to the slow reaction rate of ionic polymerizations.

The polymerizable monomers and prepolymers are not subject to any limitations. Preferably, water-soluble, physiologically safe compounds which react to become polymers swellable with water, more preferably, compounds with ethylenic double bounds, and especially compounds, the polymers of which may be degraded into compounds which can be resorbed as nutrients in the intestine, such as vinyl esters of fatty acids, amino acids or fruit acids, e.g. of lactic acid, citric acid, or tartaric acid, are selected. When polymerized, these compounds yield derivatives of polyvinyl alcohol which, under the influence of an acid or a base and/or of esterases, is cleavable into polyvinyl alcohol (PVAL) and the corresponding acid. If asparaginic acid or citric or tartaric acid or similar polycarboxylic acids are used, their di- or trivinyl esters may—on their own or in addition to monovinyl esters—be used to serve as crosslinkers. The ratio between mono- and triester monomers controls the degree of cross-linking and thus the swellability of the polymer. As, due to the reasons mentioned above, it is usually not desired for the polymer to swell too much, the amount of the cross-linker preferably is not higher than about 10 mol-%, more preferably not higher than 5 mol-%.

When prepolymers are used instead of or in addition to monomers, their tolerability and degradability also have to be taken into consideration. Preferred examples include modified representatives of natural polymers, e.g. of polypeptides, polysaccharides, and the like, as have already been mentioned above, especially vinyl-oxycarbonyloxy derivatives of gelatin, hyaluronic acid, or glycogen, i.e. carbonic monovinyl esters—e.g. those of free OH—, NH—, or $NH_2$— groups in the prepolymer—which may easily be cleaved into PVAL and the corresponding natural polymer upon decarboxylation.

In any case, the polymerization of the initiator being effective at room temperature already sets in when the components are mixed but may be suppressed to a small extent, for example, by cooling the formulation before pumping it into the endoscope's conduit or by adding small amounts of stabilizers. Nevertheless, the supply to the site of obstruction has to take place as fast as possible, i.e. under relatively high pressure and thus with a high flow rate, in order to prevent clogging of the conduit. As the composition is warmed within the body, the polymerization reaction is accelerated and proceeds quickly until completion. The polymerization product subsequently swells with water in order to form the plug representing the obstruction.

Example 8

Thermally Initiated Polymerization

A composition similar to the one described in example 7, i.e. using, for example, vinyl ester or vinyl carbonate derivatives as monomers or prepolymers, however in combination with a thermal polymerization initiator such as an organic peroxide, e.g. dibenzoyl peroxide or di-tert-butyl peroxide, or an azo-compound. At the obstruction site, the composition is immediately irradiated with infrared light via an optic fiber situated in a second conduit of the endoscope, ideally simultaneously with the formulation's exit from the first conduit, in order to initiate the polymerization before significant amounts of the composition have flown further downstream. Care has to be taken to avoid an irradiation of the intestinal mucosa in order to prevent it from being burned.

Example 9

Photopolymerization

A composition similar to those described in the two previous examples is produced using a photoinitiator and optionally an additional sensitizer or co-initiator. At the obstruction site, the formulation again is immediately irradiated, in this case with light of suitable wavelength in the UV/VIS-range as this is usually absorbed by conventional photoinitiators. The treating physician again has to take care to avoid irradiation of the surrounding intestinal mucosa in order to prevent any irritations.

Illustratively, a simple hydroxy alkyl phenone such as 2-hydroxy-2-methyl-1-phenyl-1-propanone (available as Darocur® 1173 from Ciba), which enables very high reaction rates, is used as the initiator and irradiated with light of a wavelength between 200 and 340 nm. The exact wavelength depends on the concentration of the initiator, which preferably lies between 0.001% and 0.1%, preferably in a mixture of water and an organic solvent such as water/alcohol or water/glycol (ether). Within a few seconds, the majority of the polymerizable groups are reacted, and a swollen polymer forming the desired plug is obtained.

Example 10

Polymerization Under Foaming

A composition such as the ones described in the examples 7 to 9, additionally containing a foaming agent, though, is polymerized at the obstruction site, the foaming agent causing the formed polymer to foam and thus to completely obstruct the intestinal lumen. If an azo compound is used as the initiator, the initiator itself may serve as the foaming agent, and/or one or more monomers or prepolymers contain functional groups releasing a gas in the course of the polymerization, e.g. carbonates or polyurethanes liberating $CO_2$ when decarboxylated, for example under the influence of heat, so that the polymer is blown to form a foam. Additionally, the composition may contain foam stabilizers in order to increase the stability and elasticity of the polymer foam. Examples include fatty acid alkanolamides or ethoxylated polysiloxanes.

Examples 11 to 13

Two-Component Systems

Compositions of the present invention which are curable by polymerization may also be two-component systems consisting of two formulations, A and B, the second component preferably containing the polymerization initiator, although the polymerization initiator does not have to be (the only component) contained in said second formulation. Instead of or in addition to the initiator, the second component may, for example, contain swelling agents, one or more further monomers or prepolymers, polymerization inhibitors for stopping the polymerization, protective solutions for the intestinal wall contacted by the polymerization system, or the like. Three preferred embodiments will be described below for illustrative purposes.

Example 11

The Second Component Contains a Polymerization Initiator

Here, a polymerizable composition, such as the one described in example 7, i.e. containing an initiator reactive at room temperature, e.g. the redox initiator $Fe^{2+}/H_2O_2$, is used in the form of a two-component system, formulation B containing the initiator dissolved in a minimum amount of solvent, preferably water, and formulation A containing all the other components of the composition. In a similar way as described in examples 1 and 2, the two formulations are pumped separately via two conduits of the endoscope to the obstruction site, where they are mixed, which starts the polymerization. Compared to the one-component system, which is otherwise identical, the advantage consists in the effective prevention of polymerization within the conduit, which means that more reactive initiators may be used without requiring an inhibition of the composition by means of cooling or inhibitors. The invention also encompasses cases where both formulations contain a certain amount of the same initiator or of two different initiators, for example, of a redox initiator and a photoinitiator.

Example 12

The Second Component Contains a Swelling Agent

A polymerizable composition similar to the one described in example 9, i.e. containing a photoinitiator such as 2-hydroxy-2-methyl-1-phenyl-1-propanon, but also containing a minimum amount of a solvent, preferably a mixture of water/glycol ether for dissolving all components, is pumped to the obstruction site as the formulation A and polymerized there using UV radiation. At the same time or with a delay of a few seconds, e.g. 2 or 3 seconds, pure water or a mixture of water/solvent, e.g. also water/glycol ether, is pumped to the obstruction site as the formulation B in order to guarantee a sufficient swelling of the polymer formed there. Said second formulation B may be pumped through a separate conduit of the endoscope or through the same conduit as the formulation A before, for example if the endoscope does not have three usable conduits. The advantage of such a system consists in the fact that the polymerization of the formulation A occurs even faster than in the case of example 9.

Example 13

The Second Component Contains a Protective Agent

A polymerizable formulation as described in any one of the examples 7 to 11 is pumped to the obstruction site where it is polymerized. Before that, however, the area of the intestinal mucosa around the obstruction site, e.g. 5 to 10 cm in the oral and aboral direction, respectively, is coated with a film of a protective agent in order to protect the mucosa against contact with the plug material and against any radiation. Additionally, the protective agent may act as an adhesive in order to improve the plug's adherence to the intestinal wall. Illustrative examples again include the gums mentioned above such as tragacanth and karaya, but also different other solutions, suspensions, and gels which are well tolerated by the mucosa, e.g. of gelatin, glycogen and other, preferably natural, polymers. Such a previous lining of the mucosa may also be carried out in combination with any other exemplary embodiment of the invention.

Below, different variations of removing the plug after completion of the endoscopic intervention will be described, all possible combinations of the following examples as well as of the more general measures described above being included in the scope of the present invention.

B) Different Ways of Removing the Obstruction

B1. Mechanical Removal of the Obstruction

Examples 14 and 15

Mechanical Detachment of the Plug

These examples illustrate the mere detachment of the polymer plug from the intestinal mucosa, while the subsequent ultimate removal from the intestine may principally be carried out in any suitable way.

Example 14

Pulling Off the Plug

A plug which is sufficiently stable, for example a viscous gel obtained by swelling or polymerization of gelatin or modified gelatin or a polymer foam rendered elastic using a foam stabilizer, is pulled away from the obstruction site in the aboral direction using a gripping tool at the end of the endoscope, so that the plug no longer adheres to the intestinal wall; this is sufficient in cases in which the obstruction site has been preliminarily lined with an adhesive coating and the plug material does not adhere to the mucosa to a sufficient extent without said adhesive coating. The subsequent removal from the intestine is carried out via the anus under the pressure of the following excrements and/or by dissolution by the intestinal secretion (optionally in connection with at least partial resorption).

Example 15

Application of Shear Stress

In each of the preferred cases in which the plug has been formed at the obstruction site due to its viscoelastic or thixotropic behavior, the treating physician introduces the endoscope, preferably an adequate projection thereof, into the plug and carries out a stirring movement, optionally exerting a slight pressure on the intestinal wall, in order to create a shearing effect for removing the plug. Due to the shear stress thus applied, the viscoelastic/thixotropic plug material changes back into its flowable state and, at least partially, flows away from the obstruction site, which removes the obstruction. The flowing-off may be supported by the physician by carrying out a scraping movement with the endoscope. The ultimate removal from the intestine may be carried out as in example 14, by being naturally discharged and/or at least partially dissolved and optionally resorbed. To be precise, this example constitutes a combination of a mechanical and a physical removal of the obstruction.

Examples 16 to 19

Mechanical Destruction of the Plug

Contrary to the above examples 14 and 15, in which the structural integrity of the plug is completely destroyed by mechanical means or is not destroyed at all, the following examples describe embodiments in which the plug's structure is partially destroyed by mechanical means.

Example 16

Piercing the Plug

Especially in cases in which the plug consists of a foam plastic or a gel made of a material which may be degraded in the intestine, e.g. on a polypeptide or polysaccharide basis as described above, damaging the obstruction by piercing the plug with a pin or a similar projection at the end of the endoscope is sufficient in order to remove the obstruction and to enable excrements to pass the respective site again. Subsequently, the obstruction material is gradually degraded chemically, for example enzymatically, or digested.

Example 17

Tearing Up the Plug

In cases where a plug material which, compared to example 14, is structurally less stable, but, like in example 15, is degradable in the intestine, and which adheres very strongly to the intestinal wall, for example, in the case of a gel or a foam after previous application of an adhesive, gripping the plug with a suitable tool mounted to the endoscope may also lead to the plug being torn up. This means that, after the removal of the obstruction, a more or less big part thereof still adheres to the intestinal wall and will subsequently be chemically degraded (e.g. digested).

Example 18

Cutting Up the Plug

In a similar way as in example 15, but especially in cases in which a more viscous and/or elastic, biologically degradable plug material is used, the plug may be destructed by cutting up with a scalpel or a similar cutting tool mounted to the endoscope. Modern endoscopes are commonly equipped with such tools. The removal is then preferably carried out by means of enzymatic degradation.

B2. Physical Removal of the Obstruction

Examples 19 and 20

Removing the Plug by Temperature Increase

In a similar way as in the examples 4 and 8 concerning the formation of the plug, the removal of the plug may also be carried out using irradiation with infrared light and the thus caused heating of the material.

Example 19

Removing the Plug Using the Sol/Gel Transition

A plug made of a composition similar to the one described in example 1, i.e. a gel of a natural polymer such as agar-agar, is heated by irradiation with infrared light to a temperature above the gelling temperature, for example to 45° C., which leads to a liquefaction of the material and thus to the removal of the obstruction. The ultimate removal from the intestine may again be carried out by naturally discharging the material or, preferably, by its enzymatic degradation.

Example 20

Removing the Plug by Thermal Shrinkage

A plug obtained by polymerization from a thermoresponsive hydrogel such as poly-N-isopropylacrylamide and copolymers thereof is heated by irradiation with infrared light, which causes the hydrogel to contract, liberating water, and to shrink considerably, for example by 20 to 30% of its original volume, whereafter the material may be removed in a natural way, as there is not enough water available for the material to swell again.

Examples 21 to 23

Removing the Plug by Swelling or Dissolution

As has already been explained above, the structure of gels may be significantly changed by the addition of additional swelling agents, electrolyte solutions, or solvents.

Example 21

Further Swelling

Via an endoscope conduit, additional water, preferably several times the original plug volume, for example two to three times more, e.g. 200 to 300 ml, is pumped to a plug consisting of an infinitely swellable hydrogel such as gelatin, agar-agar, or other polypeptides or polysaccharides, e.g. those described in example 1, which makes the concentration of the gel finally decrease below the threshold level required for gelling, for example 1%, and thus it liquefies.

Example 22

Shrinkage

A hydrogel, e.g. of gelatin as in example 1, is treated with an electrolyte solution such as saturated or physiological saline, which is pumped to the plug via the endoscope's conduit, which leads to a saturation of the bonding sites within the polymer with salt ions, which makes the gel contract and shrink, which in turn makes it possible to remove it from the intestine in a natural way and/or by digestion and resorption.

Example 23

Addition of a Solvent

A hydrogel, e.g. of gelatin as in example 1, is treated with a solvent, in the case of gelatin, for example, with heavily diluted acetic acid or a glycol, e.g. ethylene glycol, which is pumped to the plug via the endoscope's conduit, which leads to the gelatin being dissolved and flowing away from the obstruction site.

B3. Removing the Obstruction by Cleaving Chemical Bonds

Examples 24 and 25

Cleaving Bonds by Irradiation

The two following examples illustrate combined physico-chemical methods for cleaving bonds within the plug material.

Example 24

Irradiation with Infrared Light

In the present case, contrary to example 20, the use of infrared radiation is not intended to heat the entire plug and thus achieve a change of its structure, but to cleave temperature-sensitive chemical bonds such as azo bonds within the polymer network. For the formation of the obstruction, an azo compound, serving as a bifunctional monomer, i.e. as a cross-linker, may be copolymerized with a monofunctional "main" polymer such as a vinylester monomer or modified gelatin or modified agar-agar, using photochemical initiation (for example using Darocur® 1173). If the thus formed plug is exposed to infrared radiation after the endoscopic intervention, the azo bound is cleaved in a targeted way at the cross-linking sites, which liberates $N_2$ and leads to a substantial change of the plug's structural integrity.

On the one hand, this may cause the thus cleaved material to be no longer sufficiently swellable and thus to liquefy due to the presence of water or any other solvent or, on the other hand, the material might become more swellable due to the decreased degree of cross-linking, for example, if a high degree of cross-linking and the resulting high stiffness of the network have significantly limited the swellability before cleaving the bonds. In both cases, the subsequent supply of a swelling agent such as water may, in a similar way as in example 21, cause a dissolution of the plug material. As has already been described in some examples above, the plug material may be further cleaved by enzymes and optionally be resorbed.

Example 25

Irradiation with UV/VIS Light

This example describes cases where a photo acid generator cleavable by UV or visible light, e.g. a nitrobenzyl ester or a sulfonium or iodonium salt, is contained within the plug's polymer network. Said photo acid generator may be present in the form of an additive or, in the case of a suitable modification, integrated within the polymer structure, i.e. copolymerized. A vinyl ester or modified gelatin or agar-agar, for example, may again serve as (other) monomer; however, in this case, the presence of a comonomer with acid-labile bonds such as acetal or anhydride bonds, preferably a comonomer serving as a cross-linker, e.g. methacrylic acid anhydride or, preferably, divinyl carbonate, is obligatory. The polymerization for the formation of the plug may have been carried out thermally or using a redox initiator or a photoinitiator absorbing light at a wavelength completely different from that of the photo acid generator.

After the completion of the endoscopic intervention, the plug is irradiated with light at a wavelength absorbable by the photo acid generator in order to destroy the plug structure; thereby, an acid is liberated which causes the cleavage of the acid-labile bond, which—depending on the degree of cross-linking—may have similar consequences as described above in example 24.

Examples 26 to 28

Cleaving Bonds Using an Acid, a Base, or Enzymes

Instead of using the irradiation of a photo acid generator in order to generate acid within the plug material, an acid may also be supplied externally. In a similar way, this also holds true for other types of chemically labile bonds such as bonds cleavable by bases or enzymes.

Example 26

Addition of a Dilute Acid or Base

A plug consisting of a material similar to the one described in example 25 is treated with a preferably weak acid or base which is tolerated by the body, i.e. the solution is pumped to the obstruction site via the endoscope's conduit. Due to the effect of the acid or base, the respective labile bonds, preferably those at cross-linking sites, are cleaved, which may again lead to an increased or decreased swellability or a better accessibility for a subsequent enzymatic cleavage.

Example 27

Addition of an Enzymatic Solution

Instead of or in addition to an acid or base solution as in example 25, the plug may be treated with a solution of an enzyme acting upon the polymer network. In the case of a gelatin hydrogel, peptidases or peptide hydrolases such as amino or carboxy peptidases may be used; in the case of agar-agar or other polysaccharide gels, corresponding glycosidases may be used, e.g. galactosidases for agar-agar; and for glycoproteins and proteoglycans, mixtures comprising both enzyme types may be used. Preferably, autologous enzymes of the respective patient species, i.e. especially endogenous enzymes of the human body are used.

Example 28

Cleaving the Plug by the Intestinal Secretion

As has already been mentioned several times, especially preferred embodiments of the composition of the invention yield a plug which, optionally after previous external interference, is degradable in the natural environment of the intestine, i.e. especially under the influence of the intestinal secretion. The conditions include both the pH value of the intestinal juice which may lead to the cleavage of acid-labile bonds, less often also of base-labile bonds, as well as the enzymatic environment in the respective intestinal section which may lead to an enzymatic degradation of the plug. Preferably, the plug material is degraded to components of the patient's nutrition, which may be resorbed via the intestinal wall.

Another variation of the natural degradation in the intestine consists in a peripheral degradation, i.e. in a degradation and partial dissolution of the plug material in the area contacting the intestinal mucosa, which, on the one hand, lifts the plug's adherence to the intestinal wall, but, on the other hand, also gradually reduces the volume—in the course of the subsequent transport in the aboral direction due to the pressure exerted by the following excrements—to such an extent that the plug may be safely discharged via the anus. In this case, it is again mainly natural polymers and their derivatives, which have already been described several times herein, which may be used.

Examples 29 to 31

Model Experiments Carried Out in the Porcine Intestine

Currently are especially preferred embodiments of the present invention comprise gelling solutions of polypeptides or polysaccharides as described above in the examples 1 and 2, because, using such solutions, it may be guaranteed that the plug is formed in a way which is best tolerated by the treated patient and, at the same time, it allows for the use of exclusively natural components, especially of components which have been approved as food additives. A two-component system according to example 2 with a separate gelatinizing agent is especially preferred, as the gelling may be carried out in a highly targeted way—both, with view to the obstruction site within the intestine and to the exact point in time at which the plug is formed.

The list of polypeptides and polysaccharides which may be used is long. As examples for products approved for the use in food, only the animal proteins gelatin and casein (milk protein), which are polypeptides, and alginate (E 400-405), agar-agar (E 406), carrageen (E 407), locust bean gum (E 410), guar gum (E 412), tragacanth (E 413), gum arabic (E 414), xanthan gum (E 415), gum karaya (E 416), and pectin (E 440), which are polysaccharides, shall be mentioned, the European Union approval number of each product being specified in brackets. These products are physiologically completely safe, proteins, when used in the intestine, being partly degraded and resorbed, depending on the respective retention time, polysaccharides, on the other hand, being largely not resorbed by the body and, thus, excreted.

A series of experiments was carried out using gelatin as well as the polysaccharides carrageen and sodium alginate, which are extracted from red algae; in the course of these experiments, solutions, the concentration of which was set to a value close to the gelling point, were filled into natural intestinal sections from pigs (each about 50 cm long), which had been obtained from a slaughter house, where they were mixed with a second solution serving as gelatinizing agent in order to spontaneously form a gel plug.

Example 29

Sodium Alginate

Aqueous solutions of sodium alginate also gel spontaneously in the presence of calcium ions. The calcium ions diffuse through the spontaneously formed primary gel membrane only until the gel layer has reached a defined thickness. Sodium alginate below this gel layer does not gel and, thus, remains liquid. Thus, if aqueous sodium alginate is adequately introduced into an aqueous solution of calcium ions, a stable gel bubble is formed, the interior of which consists of non-gelled sodium alginate. The thickness of the gel membrane is determined by the initial concentration of the sodium alginate solution and by the concentration of the calcium solution. Calcium chloride constitutes the ideal choice for the calcium salt as, just like sodium alginate, it is available at pharmaceutical grade.

In order to achieve a conversion of 100% in the course of the cross-linking reaction, 0.5 mol of calcium ions are reacted with 1 equivalent of alginate. Generally, a sufficiently high amount of a solution of said calcium salt in water, at a sufficiently high concentration for a conversion of at least 20%, may be dosed into the desired area of the intestine upstream of the intended treatment site via a canula of an endoscope in order to form an area filled with liquid there.

A solution of sodium alginate at a preferred concentration of between 0.1 and 4% by weight is dosed into said area filled with liquid, which leads to the formation of said gel bubble consisting of a wall of spontaneously gelled calcium alginate and filled with non-gelled alginate salt solution. The injection of alginate solution into the gel bubble is continued until the desired obstruction, i.e. the gel plug, has been formed at the desired site.

Then, the thus formed gel bubble is of a size which leads to the temporary complete obstruction of the intestine. The gel bubble contacts the surrounding intestinal wall and forms a mechanical obstruction of the intestine. The required size of the gel bubble and, thus, the required amount of the two solutions depend on the respective situation in the target area of the intestine.

In order to facilitate the formation of the space filled with liquid, the calcium solution may be rendered highly viscous using adequate thickeners, such as starch derivatives. In order to enhance the gel bubble's adhesion to the intestinal wall, an additive promoting the adhesion to the intestinal wall (mucosa), a soluble protein, such as casein, for example, may additionally be added to the alginate solution. The two solutions may further be rendered storable by using a stabilizing agent, such as potassium sorbate.

As long as the calcium concentration in the environment of the formed gel bubble is sufficiently high, any (probably accidental, undesired) damage to the gel membrane of the gel bubble results in the outflow of non-gelled alginate solution under the immediate formation of a new gel membrane covering said damage. The discharging end of the canula of the endoscope is preferably shaped in a way that promotes the formation of the gel bubble, i.e. it is funnel-shaped or has a flared end, for example.

Specifically, 100 ml of a 1% solution of calcium chloride dihydrate ($CaCl_2.2H_2O$) were filled into a porcine intestine with a knot formed at one of its ends. Then, 50 ml of a 2% aqueous solution of sodium alginate were introduced into the calcium chloride solution via a canula introduced into the thus formed liquid body. The two solutions were at room temperature, i.e. had a temperature of 21° C., and the alginate solution was stained in a dark shade (blue) for better visualization. The calcium alginate forming spontaneously at the interface, already immediately after the introduction had started, formed a solid membrane within the liquid body of the calcium chloride solution, said membrane swelling to a gel bubble which completely obstructed the intestinal section in the course of the continued supply of alginate solution.

Figure 2:

FIG. 1 clearly shows this dark stained gel bubble as well as the remaining calcium chloride solution above it. When the intestine was turned upside down, the gel bubble firmly adhered to the intestinal wall, as is shown in FIG. 2, and remained stable when left for several hours.

Figure 3:
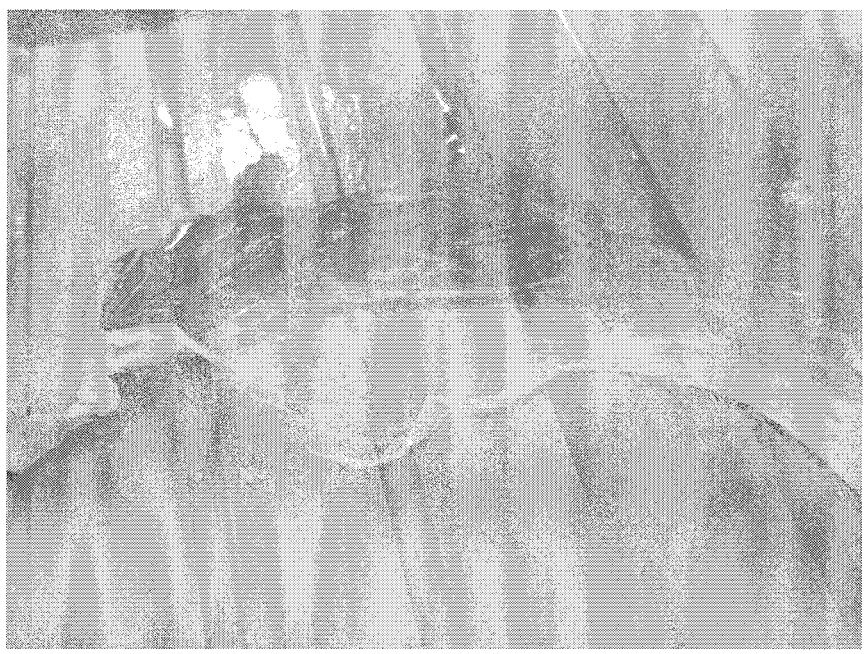

In order to remove the thus formed plug, the calcium chloride solution surrounding it was at first rinsed off with 200 ml de-ionized water. After that, the plug was pierced with a pin in order to make the non-gelled alginate solution flow out off the gel bubble. The gel membrane was then taken between two fingers and could easily be removed from the intestinal wall and pulled out of the intestinal section. FIG. 3 shows the empty gel bubble in an intestinal section cut open lengthwise, part of the gel membrane having already been removed from the intestine without having being torn apart. This example, thus, represents a combination of the above examples 2, 14, and 16.

Example 30

Carrageen

Carrageen can readily be dissolved in warm water, and, starting at a concentration of about 2% by weight, gels to form hydrogels when cooled down, which is why it would be well-suited for one-component systems as described in example 1. But, similar to alginate solutions, more diluted, cold solutions of carrageen also become cross-linked to form gels in the presence of calcium ions. In the case of carrageen, the cross-linking may also be achieved using potassium ions.

Compared to the above example 29, the way in which the reaction was carried out was reversed in order to illustrate the general efficiency of the principle of forming plugs by gelling as an embodiment of the present invention, i.e. the polysaccharide solution was introduced first into the porcine intestine, while the metal ion solution was then injected into it in order to form the gel bubble. This reversion of the order in which the solutions were introduced (which, of course, would also have worked in the previous example 29) makes use of the advantage that solutions of gelatinizing agents, such as polysaccharides and proteins, which are only slightly below the gelling point may have an increased viscosity anyway, so that no additional thickener is required in order to prevent the solution which is first introduced into the intestine from flowing away from the obstruction site.

Specifically, 100 ml of a viscous aqueous solution of carrageen at a concentration of 1% by weight were introduced into a porcine intestine, whereafter 50 ml of a 1% solution of calcium chloride dihydrate ($CaCl_2.2H_2O$) were introduced into the carrageen solution via a canula introduced into the center of the liquid body. Carrageen also cross-linked spontaneously at the interface, forming a soft, elastic gel which, again, swelled to a gel bubble obstructing the intestinal lumen when the supply of calcium chloride solution was continued. When the intestine was turned upside down, the gel also adhered firmly to the intestinal wall and remained stable when left for several hours.

After that, the carrageen solution which had not been cross-linked was rinsed off with de-ionized water, the thus formed gel plug was taken between two fingers and pulled off the intestinal wall—in this case, due to the, compared to the previous example, better adhesion of the carrageen gel—the gel membrane was torn and calcium chloride solution which had not been cross-linked flew out of it. This example, thus, represents a combination of the above examples 2 and 17.

Example 31

Gelatin

Aqueous solutions of gelatin at a concentration of about 1% by weight or more spontaneously gel at temperatures below 35° C. The same gelling effect may be achieved by a reduction of the solubility by increasing the ionic strength of the gelatin solution. As gelatin is infinitely swellable, such hydrogels may be re-dissolved by the supply of water.

Thus, 100 ml of a viscous solution of gelatin in water at a concentration of about 0.9% by weight, which had been cooled down to room temperature (21° C.), were introduced into a porcine intestine, whereafter 50 ml of a saturated saline prepared at 35° C. were introduced into the gelatin solution via a canula introduced into the center of the liquid body. The gelatin spontaneously gelled, forming a soft gel. This gel also firmly adhered to the intestinal wall, when the intestine was turned upside down, and remained stable when left for several hours.

The thus formed plug was caused to further swell by slowly supplying de-ionized water which had been pre-warmed to 40° C. (750 ml on the whole), in this way, was gradually liquefied again, and then rinsed out off the intestine. This example, thus constitutes a combination of the above examples 2 and 21.

As a result of the above model experiments, example 29, in which sodium alginate was used, turned out to be most promising. The adaptation of the two polysaccharide gels to the intestinal lumen to be obstructed by forming a gel bubble was easier than in the case of gelatin—presumably, amongst other things, due to the pressure exerted on the intestinal wall by the gel bubble, which also made it possible to achieve a tighter obstruction of the intestinal lumen. Using sodium alginate, it was easier to remove the plug from the intestinal wall than in the case of carrageen, which is probably related to carrageen's natural affinity to proteins and its thus stronger adhesion to the mucosa. For this reason, the combination of sodium alginate/$Ca^{2+}$ currently represents the most preferred embodiment of the present invention.

The present invention, thus, provides several new compositions which may be used, in different, but simple and efficient ways, for the formation of a temporary obstruction of the intestine in order to be able to carry out an endoscopic intervention unimpededly, said obstruction being removable in several different ways after the completion of the intervention. For the formation of the obstruction, conventional endoscopes may be used.

The invention claimed is:

1. A method for forming a temporary obstruction of the intestine of a mammal, said method comprising the steps of:
   providing a composition in a nonflowable state, which composition has a viscoelastic or thixotropic behavior,
   preliminarily converting said composition into a flowable state by supplying mechanical energy thereto,
   transporting said composition in said flowable state via the anus into the intestine of the mammal by pumping the composition through a conduit of an endoscope to the site of the obstruction at such a pressure and flow rate that the resulting shear stress provides sufficient energy in order to maintain the flowability of the composition,
   solidifying said composition by removing the supplied energy to form a solid plug at a desired site of the intestine,
   subsequently changing the structure of the plug in order to at least partially remove said obstruction from the intestine of the mammal.

2. The method according to claim 1, wherein said composition is a thixotropic solution, suspension, or dispersion of at least one natural or synthetic polymer.

3. The method according to claim 1, wherein the solidification of said composition comprises one or more additional processes selected from the group consisting of swelling or coagulation, polymerization, and cross-linking.

4. The method according to claim 3, wherein said one or more additional processes includes swelling in water or in a aqueous mixed solvent.

5. The method according to claim 1, wherein said composition is solidified to form a solid foam or gel.

6. The method according to claim 1, wherein the step of changing the structure of the plug in order to at least partially remove said obstruction comprises at least partially destroying the plug by mechanical, physical, and/or chemical means.

7. The method according to claim 1, wherein the structure of the plug is at least partially destroyed by swelling or further swelling.

8. The method according to claim 1, wherein the structure of the plug is at least partially destroyed by being irradiated with electromagnetic radiation.

9. The method according to claim 1, wherein the structure of the plug is at least partially destroyed by cleaving chemical bonds.

10. The method according to claim 2, wherein the polymer contains labile bonds and the structure of the plug is at least partially destroyed by cleaving said bonds.

11. The method according to claim 2, wherein labile bonds are created within the plug during polymerization and/or cross-linking of the polymer and the structure of the plug is at least partially destroyed by cleaving said bonds.

12. The method according to claim 11, wherein the labile bonds are selected from hydrolysis-, light- and temperature-sensitive bonds and enzymatically cleavable bonds.

13. The method according to claim 11, wherein the labile bonds are selected from the group consisting of acetal, ketal, ester, ortho-ester, azo, ether, and anhydride bonds.

14. The method according to claim 1, wherein the solid plug is removed via the anus, optionally after a preceding, at least partial, destruction of its structure.

15. The method according to claim 1, wherein, by cleaving chemical bonds, the solid plug is converted into cleavage products which are removed by being resorbed by the intestinal wall.

16. The method according to claim 1, wherein the mammal is a human being.

17. The method according to claim 6 wherein said mechanical means for at least partially destroying said obstruction comprises supplying mechanical energy to the obstruction to convert the composition into a flowable state again.

* * * * *